United States Patent [19]

Tunc

[11] 4,005,251
[45] Jan. 25, 1977

[54] PROCESS FOR PREPARATION OF ALKALI CELLULOSE ESTER SULFATES

[75] Inventor: Deger C. Tunc, East Brunswick, N.J.

[73] Assignee: Johnson & Johnson, New Brunswick, N.J.

[22] Filed: Feb. 20, 1975

[21] Appl. No.: 551,570

Related U.S. Application Data

[62] Division of Ser. No. 431,455, Jan. 7, 1974, Pat. No. 3,897,782.

[52] U.S. Cl. .............................. 536/59; 128/290 R
[51] Int. Cl.² ......................................... C08B 7/00
[58] Field of Search ................ 260/215, 227, 230; 536/59

[56] References Cited
UNITED STATES PATENTS

| | | | |
|---|---|---|---|
| 2,582,009 | 1/1952 | Crane | 260/215 |
| 2,849,330 | 8/1958 | Hoffman et al. | 260/215 |
| 3,335,128 | 8/1967 | Hiatt et al. | 260/215 |
| 3,624,069 | 11/1971 | Schweiger | 260/215 |
| 3,702,843 | 11/1972 | Schweiger | 260/215 |

Primary Examiner—Ronald W. Griffin

[57] ABSTRACT

A barrier film is provided for a product used in contact with body fluids. The barrier film comprises an alkali salt of a sulfated cellulose ester, with a degree of sulfate substitution satisfactory to render the film resistant to body fluids and yet dispersible in low salt concentration aqueous solutions such as those found in a household water closet. There is also disclosed a process for preparing alkali salts of sulfated cellulose esters comprising sulfating woodpulp, acylating the sulfated wood pulp, and precipitating the desired product in an aqueous precipitation medium maintained at a specified pH range.

7 Claims, 6 Drawing Figures

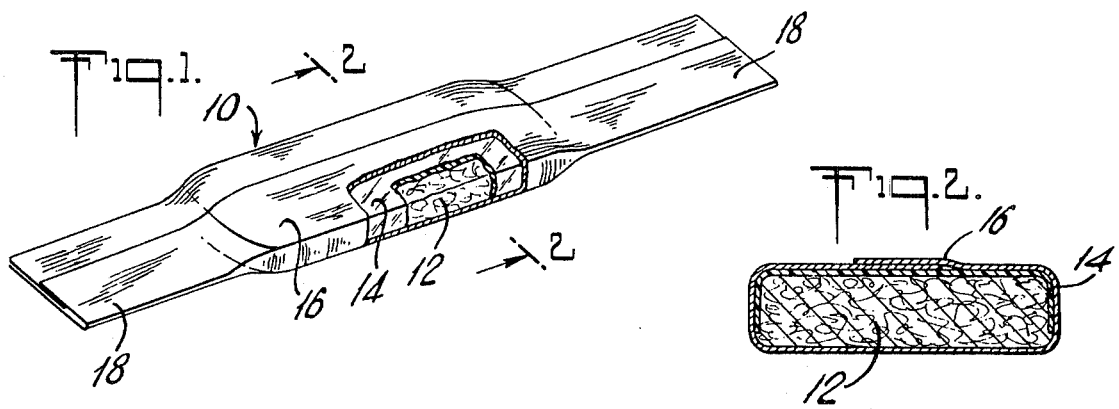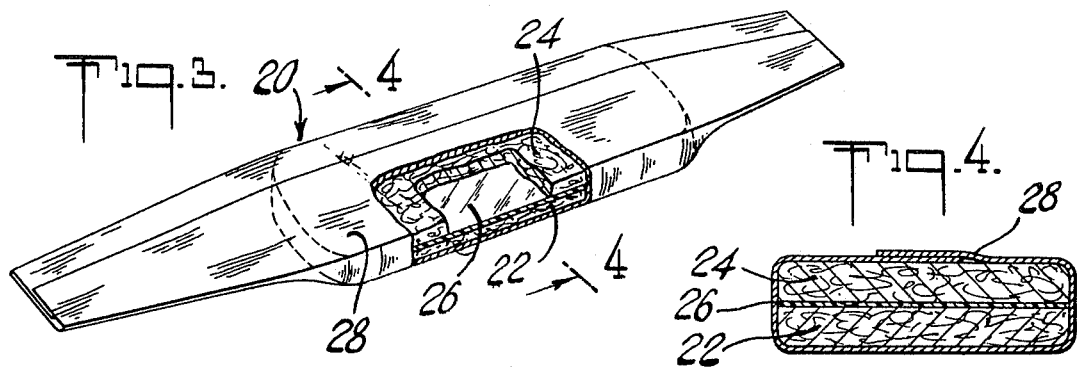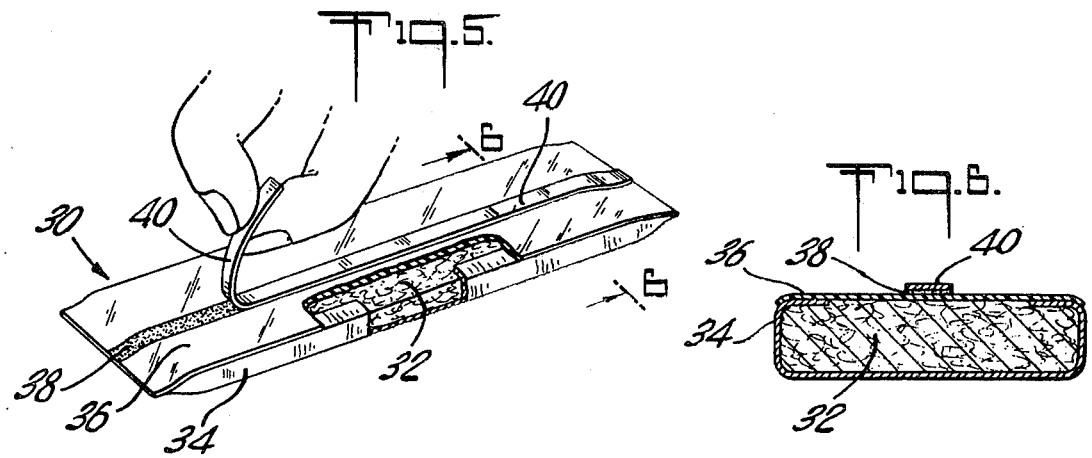

PROCESS FOR PREPARATION OF ALKALI CELLULOSE ESTER SULFATES

This is a division of application Ser. No. 431,455 filed Jan. 7, 1974, now U.S. Pat. No. 3,897,782.

BACKGROUND OF THE INVENTION

This invention concerns the incorporation of protective barrier films in products to be contacted in use with fluids exuded from the body such as blood, menstrual fluid and urine. Specifically, the barrier films of this invention are useful in connection with absorbent products such as sanitary napkins, diapers, dressings and the like and are likewise useful as liners for ostomy bags, bedpans, and other receptacles for body exudates. The films exhibit adequate tensile strength and retain their structural integrity when in contact with the aforesaid body fluids, and are still readily dispersible in water so that the film or the combination of film and product may be disposed of in an ordinary water closet.

Heretofore, the choice of suitable barrier films has been extremely limited in that those properties desirable in films used for this purpose, are infrequently found in combination. For example, the barrier film must be sufficiently strong to resist disintegration for a reasonable period of time when in use, i.e., the films must be insoluble or at least only slightly soluble in body fluids and must exhibit substantial tensile strength when subjected to such fluids. In conflict with this criterion, it is important that the barrier film be readily dispersible in water so that the absorbent product can be conveniently flushed away. Heretofore, barrier films have been incapable of adequately meeting both criteria.

A suitable barrier film must also have sufficient abrasive strength to withstand wear and tear when the product is one which is to be worn, such as a dressing, a sanitary napkin or a diaper, and at the same time, must be adequately soft and flexible so as to be comfortable and not exhibit the noise or rattling frequently associated with tough resinous films. Once more, these criteria are in conflict and a material suitably possessing both properties has heretofore been unknown.

Finally, a body fluid barrier film, especially if it is used in disposable products, should be inexpensive. The barrier films of this invention are inexpensive as they may be made from woodpulp which is readily and economically available.

SUMMARY OF THE INVENTION

In accordance with this invention, a barrier film is provided, in a product for contacting body fluids, which is dispersible in water and resistant to said body fluids, said barrier film comprising a film of an alkali salt of a sulfated cellulose ester. Preferably the sulfated cellulose ester is chosen from the group consisting of alkali cellulose ester sulfates wherein the acyl group comprises from 1 to 6 carbon atoms; more preferably the acyl group comprises from 1 to 4 carbon atoms.

Examples of these resins are such alkali cellulose ester sulfates as sodium, potassium or lithium cellulose acetate sulfate, sodium, potassium or lithium cellulose acetate-butyrate sulfate, sodium cellulose propionate sulfate and potassium cellulose butyrate sulfate. Most preferably the barrier film of the present invention comprises sodium cellulose acetate sulfate. If so desired, the films may comprise mixtures of the various alkali cellulose acylate sulfates above mentioned.

It has now been discovered that these resinous films exhibit the unusual properties of retaining their tensile strength in salt solutions such as body fluids while readily dispersing in tap water. It has further been discovered that these unique properties are a function of the degree of sulfate substitution (hereinafter, "D.S.") which expresses the average number of sulfate groups per anhydroglucose unit of the cellulosic ester. In general, by increasing the D.S. of a particular resin, the films cast therefrom will exhibit increasing dispersibility in water and decreasing strength in salt solutions. It has been discovered that by utilizing resins having a D.S. varying from about 0.1 to about 0.45, a barrier film used, for example, as a protective barrier in an absorbent product such as a sanitary napkin or diaper or, alternatively, as a liner for a bedpan or ostomy bag, will exhibit sufficient strength in body fluids and will readily disperse in water. Preferably, the D.S. should range from about 0.15 to about 0.40, and more preferably from about 0.27 to about 0.36.

The resins used in the products of this invention have been found to be compatible with readily available plasticizers which may be incorporated into the barrier film to produce a relatively noiseless, comfortable product such as an absorbent napkin or diaper without affecting its ability to disperse in water. Various other additives, such as fillers, coloring agents, and stabilizing agents may also be included in the barrier films of this invention.

According to the present invention there are also provided novel methods for the preparation of alkali salts of sulfated cellulose esters. Formerly such resins were precipitated from solution in the reaction medium in which they were prepared by treatment with various organic solvents, particularly isopropanol. This method is economically unattractive because it requires either that costly organic solvent be lost during processing or that expensive solvent recovery equipment be purchased and installed. It has now been found that alkali cellulose ester sulfates may be economically and safely recovered from solution in the reaction mixture in which they were prepared by precipitation in an aqueous medium maintained at a pH between about 3 and about 8, and preferably at a pH of from about 3.5 to about 5.5. The required pH range may be achieved by adding a base to the aqueous precipitation medium. As will be seen, this method of precipitation may be employed for solutions of alkali salts of sulfated cellulose esters in substantially non-aqueous systems regardless of the method by which the cellulose was sulfated and/or acylated.

BRIEF DESCRIPTION OF THE DRAWINGS

FIG. 1 is a perspective view of a sanitary napkin embodying this invention with parts broken away to show the interior construction thereof;

FIG. 2 is a cross-sectional view taken approximately along lines 2—2 of FIG. 1;

FIG. 3 is a perspective view of a second sanitary napkin embodying this invention with parts broken away to show the interior construction thereof;

FIG. 4 is a cross-sectional view taken approximately along lines 4—4 of FIG. 3;

FIG. 5 is a perspective view of an absorbent pad or undergarment liner embodying this invention with parts broken away to show the interior construction thereof; and FIG. 6 is a cross-sectional view taken approximately along lines 6—6 of FIG. 5.

DETAILED DESCRIPTION OF THE INVENTION

The sulfated cellulose esters used to form the barrier films of this invention may be produced by first forming the sulfate derivative of cellulose and then esterifying with a suitable acylating agent.

The sulfated cellulose is prepared by slurrying cellulose, for example in the form of woodpulp, in an inert liquid reaction medium such as glacial acetic acid and reacting the cellulose slurry with a sulfating mixture prepared from reactants comprising acetic anhydride, an alkali sulfate, glacial acetic acid and sulfuric acid. The sulfated cellulose so obtained is then acylated with an acylating agent such as acetic anhydride to form a solution of the desired alkali cellulose acylate sulfate in the reaction mixture. The cellulose ester sulfate is then precipitated from solution by adding the reaction mixture in which it is dissolved to an aqueous precipitation medium maintained at a pH of from about 3 to about 8. The pH of the aqueous precipitation medium is maintained within the specified range by the addition, as necessary, of suitable amounts of an aqueous base. Examples of suitable bases are the alkali metal hydroxides such as sodium, potassium or lithium hydroxide; the salts of alkali metal hydroxides with weak acids, such as sodium carbonate, potassium carbonate, and lithium acetate; and ammonium hydroxide.

Alternatively, solutions of alkali salts of sulfated cellulose esters may be prepared by dissolving a commercially available cellulose ester in an inert liquid reaction medium and then sulfating the cellulose ester with alkali acetyl sulfate or with other well known procedures. The alkali cellulose esters sulfate may then be recovered by precipitation in an aqueous precipitating medium in the manner described above.

Films may be cast by dissolving the resins in a suitable solvent, applying the solution onto a release surface and allowing the solvent to evaporate. The film is then peeled from the release surface. A wide variety of solvents may be used including water; mixtures of water with acetone, methyl ethyl ketone or methylene chloride; or mixtures of methanol with acetone, methyl ethyl ketone or methylene chloride. The resin concentrations are limited, on the one hand, by the necessity for maintaining the solution sufficiently dilute so as to exhibit good fluidity and, on the other hand, by the necessity for maintaining the solution sufficiently concentrated so as to limit the volume to be handled to a convenient quantity. In general, it has been discovered that films having thicknesses varying from 0.1 to 5.0 mils can conveniently be prepared from solutions containing about 1 to about 10 percent by weight of the alkali salt of the sulfated cellulose ester and preferably from solutions containing about 2 to 5 percent by weight of the cellulose resin. Suitable release surfaces for casting film include glass and Teflon coated surfaces. For example, excellent translucent, peelable films are obtained from an alkali salt of a sulfated cellulose ester resin dissolved in a 3:1 (by weight) mixture of acetone and water and cast, at room temperature, onto a Teflon coated pan.

Films cast from the alkali salts of sulfated cellulose ester are suited for use as flushable barrier films in a product used in contact with such body fluids as blood, menstrual fluid, urine, and similar body exudates. These fluids, in general, exhibit properties which, with respect to the films, are analogous to aqueous salt solutions having a salt content which varies from about 0.8 to about 1.5 percent by weight of sodium chloride. On the other hand, tap water normally supplied to water closets and the like generally has an extremely low salt concentration of less than about 250 parts per million of chloride ion. It has been discovered that the alkali salts of sulfated cellulose esters of this invention maintain their integrity for a substantial period of time in solutions having a salt concentration exhibiting the properties of body fluids, whereas, surprisingly, they display a far lower resistance to dispersion in tap water. It has further been discovered that by modifying the D.S. of these resins, the salt resistances and water dispersibility of the films can be modified to suit the particular purposes of this invention, i.e., films may be made which will adequately provide a barrier for body fluids for a suitable length of time and which may be flushed away in a water closet.

Specifically, by lowering the degree of sulfation, the barrier films of this invention become more resistant to salt solutions in that they retain their integrity after being subjected to these solutions for longer periods of time and that they exhibit higher tensile strengths when subjected to a given salt concentration for a given period of time. In general, if the D.S. is maintained at below about 0.4, an adequately salt resistant film results. Preferably, the D.S. should be maintained at below about 0.38 and more preferably below about 0.36. While the resistance of the films to salt solutions having a salt concentration exhibiting the properties of body fluids increases greatly with decreasing D.S., the ability to disperse readily in tap water is maintained until extremely low D.S. values are reached. Adequate tap water dispersibility is achieved when the D.S. is maintained at a value of at least about 0.15. Preferably, the D.S. should be at least about 0.27.

The barrier films of this invention are highly compatible with a great variety of plasticizers which may be incorporated therein to improve such characteristics of the film as flexibility and resistance to abrasion, and to reduce "noise", i.e., the rattle resulting from the flexing of the film. These properties are particularly important when the barrier films are used in connection with items to be worn such as the aforementioned sanitary napkins, diapers and the like. Water soluble plasticizers such as glycerol and the polyethylene glycols are suitable, as well as such water-insoluble plasticizers as castor oil.

When the films of this invention are used in connection with such products as liners for bedpans, ostomy bags, and other receptacles for body fluids, they may be cast directly on the inside surface of the receptacle prior to use or may alternatively be precast and then applied to the receptacles. In use, after fluid has been deposited into the lined receptacle, the entire liner, including the deposited fluid may be lifted out of the receptacle and deposited in a water closet. The films of this invention will exhibit sufficient tensile strength when in contact with the deposited fluid to allow the liner to be lifted out of the receptacle and will at the same time be completely dispersible in a water closet so as to be flushable.

Referring now to FIGS. 1 and 2 of the drawing, illustrated therein is an embodiment of the films of this invention as used with a sanitary napkin 10. The napkin comprises an absorbent core 12 of fibrous material such as comminuted wood pulp fibers, cotton linters, rayon fibers, cotton staple, bleached sulfite linters, other cellulosic or modified cellulosic fibers and the like. Overlying the bottom surface of the absorbent core (that portion of the napkin worn away from the body) is a thin barrier sheet 14 comprising the films of this invention. A fluid pervious cover 16 surrounds the absorbent core 12 and the barrier sheet 14 with the lateral edges thereof overlapped and secured on the bottom surface of the napkin 10. The cover 16 can be extended beyond the ends of the core 12 to form the usual attachment tabs 18. While FIGS. 1 and 2 illustrate a tabbed napkin, it will be understood by one skilled in the art that the advantages accruing to the use of barrier films of this invention are equally applicable to a tabless product, e.g., one where tabs are not used as attachment means, or where other attachment means such as, for example, adhesive means, are used.

As incorporated into the product described in FIGS. 1 and 2, the barrier sheet, comprising films of this invention, is uniquely suited to preclude the passage of menstrual fluid through the core to the bottom surface of the napkin. Menstrual fluid, as other body fluids, exhibits properties, with respect to the film, which are analogous to an aqueous solution having a salt content of about 0.8 to about 1.5 percent by weight and it is within these concentrations that the films of this invention are resistant and impermeable. Notwithstanding the resistance of the films to menstrual fluid, when the films are introduced into an aqueous low salt concentration solution, they are dispersible. Accordingly, by employing a water dispersible material for the cover 16 (and a water dispersible core 12) the sanitary napkins of FIGS. 1 and 2 may be completely disposed of in a water closet. Alternatively, the illustrated napkin may be provided with a non-water dispersible cover, in which event the cover would first be removed and the pad and barrier film dropped into a water closet for disposal. In either event, the unique barrier film of this invention will completely disperse in a water closet under the swirling action of the water found therein, and will in no way clog or otherwise impair the operation of the water closet and associate plumbing.

FIGS. 3 and 4 illustrate a second embodiment of this invention in a napkin of alternative construction. A sanitary napkin 20 is provided with first and second absorbent layers 22 and 24. Sandwiched therebetween is a barrier sheet 26 comprising the film of this invention. A fluid pervious cover 28 surrounds the absorbent layers 22 and 24, with the lateral edges thereof overlapped and secured on the bottom surface of the napkin 20. As in the prior described embodiment, the cover is illustrated as extending beyond the absorbent layers to form attachment tabs, although it is equally advantageous to use the teachings of this invention in a tabless product. Again the films of this invention are uniquely suited for use as barrier films and while they will preclude the passage of menstrual fluid to the bottom of the napkin, they are completely dispersible in a water closet. Hence, if the napkin 20 is provided with a water dispersible cover, it may be completely disposed of by flushing or, alternatively, if the napkin is provided with a non-water dispersible cover, the cover may be first removed and then the remainder of the napkin may be disposed of by flushing. A particular advantage of a napkin having the construction illustrated in FIG. 20 is that the barrier film located between absorbent layers is less likely to exhibit "noise" which could embarrass the wearer and hence the need for the addition of plasticizers to the film is lessened.

In this connection, it will be apparent to one skilled in the art that, while two separate absorbent layers have been illustrated, many alternatives are possible, such as, for example, the use of multiple layers or the forming of the layers by simply folding a single sheet of absorbent material.

FIGS. 5 and 6 illustrate still another embodiment of this invention. Illustrated therein is an absorbent pad 30 which is useful as a protective cover for undergarments. The pad is provided with an absorbent core 32. A fluid pervious cover 34 overlies the top (the surface worn against the body) and side portions of the core, the lateral edges also overlying the peripheral portions of the bottom surface of the core. A barrier film 36, in accordance with this invention, is provided to overlie the bottom surface of the core and those portions of the cover 34 overlying the bottom surface. The barrier sheet 36 and the cover 34 are secured together and preferably, are secured to the core. The outer surface of the barrier sheet is provided with adhesive means 38 which may be, for example, a layer of pressure sensitive adhesive or a double-faced adhesive tape. The adhesive means 38 is protected, prior to use by a strippable peelable cover 40. In use, the cover 40 is stripped from the napkin exposing the adhesive means. The napkin is then placed, for example, in the crotch portion of a panty and held in place by adhering the barrier film portion to the panty with the adhesive means. Once again, the unique features of the barrier film allow the pad to be readily disposed of by flushing in a water closet.

In order to better illustrate the invention, the following examples are given:

EXAMPLE 1

This Example describes the preparation of a water dispersible, salt solution insoluble cellulose ester sulfate resin according to a process which comprises slurrying the cellulose (in the form of woodpulp) in an inert organic liquid, sulfating the cellulose by reacting the cellulosic slurry with a sulfating mixture comprising an alkali acetyl sulfate, esterifying the sulfated cellulose in a reaction mixture comprising the inert organic liquid, sulfated cellulose and an acylating agent and precipitating the desired alkali cellulose acetate from solution in said reaction mixture by combining said reaction mixture with an aqueous precipitation medium maintained at a specified pH range.

400 grams of woodpulp (ITT Rayoniers Placetate-F) was ground and added to 2000 grams of glacial acetic acid to form a slurry which was tumbled in a closed cylindrical reactor for 20.5 hours at 24° C.

A sulfating mixture comprising sodium acetyl sulfate was prepared as follows: 162.9 grams acetic anhydride and 52.5 grams glacial acetic acid were added to a 1 liter jacketed resin flask. 30.8 grams of sodium sulfate were added and the contents stirred for 5 minutes. 20.15 grams of concentrated sulfuric acid (98% by weight) were added dropwise at such a rate that the temperature of the reactor contents did not exceed 55° C. The rate of addition of sulfuric acid may be increased, if desired, if cooling is applied by circulating ice water through the jacket of the reactor. The reactor was stirred for 30 minutes after the addition of the sulfuric acid was completed.

The slurry of woodpulp in glacial acetic acid was transferred to a jacketed, double planetary mixer (Ross reactor) equipped with a thermometer and a stirrer and was cooled to 18° C. The sulfating mixture was added to the Ross reactor at a rate such that the temperature of the contents did not exceed 32° C. The use of external cooling permits faster addition of the sulfating mixture. Stirring was continued for 30 minutes after the addition of the sulfating mixture has been completed. 112.0 grams of concentrated sulfuric acid were then added to the Ross reactor at a rate such that the temperature of the contents did not exceed 32° C.

The sulfated cellulose was then acylated by adding 1080 grams of acetic anhydride, pre-cooled to −10° C to the contents of the Ross reactor, the temperature in the reactor being maintained below 32° C during this addition. When the addition of the acetic anhydride was completed, stirring was continued and the temperature of the contents of the Ross reactor was maintained at 32° C, until 2 hours, counting from the time the acetic anhydride addition was begun, had elapsed.

In order to precipitate the sodium cellulose acetate sulfate from solution in the reaction mixture, the reaction mixture was added to an aqueous precipitation medium comprising 6000 mls. of water, cooled to 5° C. The pH of the aqueous precipitation medium was maintained at a pH of 5.3 during the precipitation procedure by simultaneously adding a 50% by weight solution of aqueous sodium hydroxide. The aqueous precipitation medium was stirred and cooled during the addition of the sodium hydroxide solution and the reaction mixture thereto, and the product precipitated in the form of a fine powder. The precipitated resin was recovered from the aqueous precipitation medium by filtering in a Buchner funnel and was dried at 53° C. Taking advantage of the fact that the desired cellulose ester sulfate is substantially less soluble in cold water than hot, the precipitated product, after grinding in a Wiley mill, was washed with 5000 mls. of water cooled to 5° C, after which the product was isolated by filtration. The washing and isolation steps were repeated four times. Upon completion of the wash steps, the product was filtered and dried at 53° C.

528.9 grams of sodium cellulose acetate sulfate were recovered. Analysis gave the following results: 3.82% by weight sulfur, corresponding to a degree of substitution of $SO_4^=$ of 0.36; 1.81% by weight sodium; 34.51% by weight acetyl

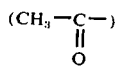

corresponding to a degree of acetyl substitution of 2.40. 6.25 grams of the final product were dissolved in 93.75 g. of a 3:1 weight mixture of acetone and water to form a clear solution. The solution was cast on a piece of silicone release paper and the solvents evaporated. The resulting film was translucent and had good flexibility.

EXAMPLE 2

A series of sodium cellulose acetate sulfates, designated 2A, 2B, 2C, and 2D, were prepared by the method described in Example 1 by varying the amounts of the sulfating mixture used and by varying the quantities of acetic anhydride and sulfuric acid comprising the acetylation mixture. The pH maintained during the precipitation step is indicated in Table I. The resulting sodium cellulose acetate sulfate resins had the degrees of substitution of sulfate ($SO_4^=$) and acetyl

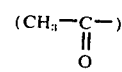

groups as shown in Table I.

A series of films were cast from the resins of Examples 1 and 2 and tested in water, 0.9% by weight aqueous NaCl, and 2.0% by weight NaCl, to determine their ability to maintain their structural integrity. Two tests were employed. In the first, called the Fast Break-Up Test, a 3 cm. × 3 cm. × 2 mil film of each of the resins to be tested was placed in a 250 ml. beaker containing 150 mls. of the desired test liquid. The test liquids were stirred with a 1½ inch Teflon coated bar magnet driven by a Precision Scientific Mag-Mix magnetic stirrer operating at 115 volts. The samples to be tested were put into the stirred test solution and the time in seconds ("break-up time") required for the sample to disintegrate was measured. The second test, called the Slow Break-Up Test, was the same as the first test except the Teflon coated bar magnet was rotated at 90 rpm by adjusting the operating voltage of the magnetic stirrer. The break-up times of films prepared from the various resins of Examples 1 and 2 are recorded in Table II.

The films are further tested to determine their respective tensile strength when subjected to various liquids for various periods of time. Film samples measuring three inches by one inch were immersed in the desired test liquid for the specified period of time and then immediately tested in an Instron machine, at a jaw separation of 2 inches and a crosshead speed of 2 inches per minute. The results of these tests, as well as dry tensile strengths, are reported in Table III. Test results are reported in pounds per square inch.

TABLE I

| SAMPLE | SULFATING MIXTURE - GRAMS USED | | | | ACETYLATING MIXTURE - GRAMS USED | | pH of AQUEOUS PRECIPITATION MEDIUM | DEGREES OF SUBSTITUTION | | |
|---|---|---|---|---|---|---|---|---|---|---|
| | $(Ac)_2O$ | HAc | $Na_2SO_4$ | $H_2SO_4$(98%) | $(Ac)_2O$ | $H_2SO_4$(98%) | | $SO_4^-$ |  | OH |
| 2A | 217 | 70 | 41.1 | 26.9 | 1080 | 100 | 5.2 | 0.42 | 1.87 | 0.71 |
| 2B | 162.9 | 52.5 | 30.8 | 20.15 | 1080 | 112 | 5.2 | 0.34 | 2.57 | 0.09 |
| 2C | 162.9 | 52.5 | 30.8 | 20.15 | 1080 | 112 | 5.45 | 0.27 | 2.62 | 0.11 |

TABLE I-continued

| SAMPLE | SULFATING MIXTURE - GRAMS USED | | | | ACETYLATING MIXTURE - GRAMS USED | | pH of AQUEOUS PRECIPITATION MEDIUM | DEGREES OF SUBSTITUTION | | |
|---|---|---|---|---|---|---|---|---|---|---|
| | (Ac)₂O | HAc | Na₂SO₄ | H₂SO₄(98%) | (Ac)₂O | H₂SO₄(98%) | | $SO_4^=$ | $CH_3-\overset{O}{\underset{\|}{C}}-$ | OH |
| 2D | 122 | 39.4 | 23.1 | 15.1 | 1080 | 60 | 5.2 | 0.15 | 1.97 | 0.88 |

All parts are parts by weight per 400 parts of woodpulp
(Ac)₂O = acetic anhydride;
HAc = acetic acid.

TABLE II

| | DEGREE OF SUBSTITUTION | | BREAK-UP TIMES | | | | | |
|---|---|---|---|---|---|---|---|---|
| | | | SLOW BREAK-UP TEST | | | FAST BREAK-UP TEST | | |
| SAMPLE | $SO_4^=$ | $CH_3-\overset{O}{\underset{\|}{C}}-$ | DISTILLED WATER | 0.9% Aq.NaCl | 2.0% Aq.NaCl | DISTILLED WATER | 0.9% Aq.NaCl | 2.0% Aq.NaCl |
| Example 1 | 0.36 | 2.40 | 328 secs. | >3 hrs. | >50 hrs. | 39 secs. | 92 secs. | 175 secs. |
| Example 2A | 0.42 | 1.87 | 58 secs. | 75 secs. | — | 7 secs. | 10 secs. | 13 secs. |
| Example 2B | 0.34 | 2.57 | 1620 secs. | >24 hrs. | >24 hrs. | 23 secs. | 135 secs. | 540 secs. |
| Example 2C | 0.27 | 2.62 | — | — | — | 23 secs. | 100 secs. | 215 secs. |
| Example 2D | 0.15 | 1.97 | * | — | — | 64 secs. | 302 secs. | 498 secs. |

\* = over 24 hours
— = did not test

The results of the break-up time tests (Table II) and the tensile strength tests (Table III) show that the resinous films prepared from sulfated cellulose esters having the indicated degrees of sulfate and acetyl substitution have a greater resistance to aqueous salt solutions than to distilled water. The data show that the optimum combination of water dispersibility and salt solution insolubility occurs at degrees of sulfate substitution ranging from about 0.27 to about 0.36. At degrees of sulfate substitution above about 0.36, water dispersibility is excellent but tensile strength is somewhat reduced. At degrees of sulfate substitution below about 0.27, water dispersibility is somewhat reduced while tensile strength in aqueous salt solutions is improved.

EXAMPLE 3

This example illustrates that films can be prepared from mixed esters of alkali cellulose sulfates which have good tensile strength and structural integrity in sodium chloride solutions and yet are dispersible in plain water. Sodium cellulose acetate butyrate sulfate is prepared as follows:

113.5 grams of alcohol soluble cellulose acetate butyrate (available from Eastman Kodak) was dissolved in 463 grams of glacial acetic acid. A sulfating mixture comprising 34.5 grams of glacial acetic acid, 107.0 grams of acetic anhydride, 21.25 grams of sodium sulfate, and 13.22 grams of sulfuric acid was prepared using the method described for preparing the sulfating mixture of Example 1.

TABLE III

| | TENSILE STRENGTH (lbs. per square in.) | | | | | | | | | | | | | | | |
|---|---|---|---|---|---|---|---|---|---|---|---|---|---|---|---|---|
| SAMPLE | DRY | DISTILLED WATER (Minutes) | | | | | | | | 0.9% AQUEOUS NaCl (Minutes) | | | | | | |
| | | ½ | 1 | 3 | 5 | 10 | 20 | 30 | 120 | ½ | 1 | 3 | 5 | 10 | 20 | 30 | 120 |
| Example 1 | 7479 | 225 | 169 | 50 | * | * | * | * | * | 506 | 441 | 261 | 414 | 336 | 373 | 291 | 271 |
| Example 2A | 7149 | * | * | * | * | * | * | * | * | 20 | * | * | * | * | * | * | * |
| Example 2B | 9000 | 391 | 245 | 148 | 104 | 47 | 42 | 41 | — | 804 | 807 | 559 | 621 | 626 | 553 | 513 | 526 |
| Example 2C | 8815 | 206 | 184 | 215 | 97 | — | — | 143 | 133 | 923 | 674 | 668 | 604 | — | — | 609 | 544 |
| Example 2D | 5112 | — | — | — | — | — | — | 497 | 593 | — | — | — | — | — | — | 1113 | 1136 |

| SAMPLE | 2.0% AQUEOUS NaCl (Minutes) | | | | | | | |
|---|---|---|---|---|---|---|---|---|
| | ½ | 1 | 3 | 5 | 10 | 20 | 30 | 120 |
| Example 1 | 953 | 693 | 822 | 732 | 687 | 773 | 658 | 815 |
| Example 2A | 40 | 23 | * | * | * | * | * | * |
| Example 2B | — | — | — | 982 | 949 | 906 | 1124 | 1098 |
| Example 2C | 1078 | 1193 | 1063 | 1034 | — | — | 1066 | 710 |
| Example 2D | — | — | — | — | — | — | 1514 | 1608 |

\* = Sample broke-up prior to testing
— = Did not test

The solution of cellulose acetate butyrate in glacial acetic acid was transferred to a Ross reactor and reacted with the above described sulfating mixture according to the procedure for sulfation given in Example 1. When the sulfation step was completed, the sulfated cellulose mixed ester was dissolved in the reaction mixture in the Ross reactor. The product was precipitated by adding the reaction mixture to an aqueous precipitation medium maintained at pH=6.4 with aqueous sodium hydroxide. The cellulose ester sulfate was then washed and dried according to the procedure given in Example 1.

The final product comprised sodium cellulose acetate butyrate sulfate and had the following composition: 4.89% sulfur by weight; 24.63% by weight (acetyl + butyryl) determined as acetyl; and 40.67% by weight (acetyl + butyryl) determined as butyryl.

A film was cast from a 6.25% by weight solution of the final product in a 3:1 weight mixture of acetone and water. The film so cast completely dissolved in water within 30 minutes but did not dissolve in 2% by weight aqueous NaCl even after 6 days.

by increasing the amount of sulfating mixture used for a constant amount of cellulose.

EXAMPLE 6

In order to demonstrate the effect of varying the amounts of acetic anhydride and sulfuric acid used in the acetylation step, two samples (designated 6A and 6B) of sodium cellulose acetate sulfate were prepared using the procedure of Example 1 but varying the amounts of sulfuric acid and acetic anhydride used during acetylation. The reagents, and their amounts, used in the sulfating mixture were the same for Example 1 and the present example. Table V shows the variations made in the amounts of the reagents in the sulfating mixture along with the analysis of the resulting products.

TABLE V

| SAMPLE | AMOUNT OF ACETIC ANHYDRIDE | AMOUNT OF SULFURIC ACID | RESULTING PRODUCT | | |
|---|---|---|---|---|---|
| | | | % S | % Na | % Acetyl |
| 6A | 111.6 | 24.79 | 2.52 | 1.80 | >1.0 |
| 6B | 270.0 | 50.0 | 2.99 | 2.14 | 7.14 |
| Example 1 | 1080.0 | 112.0 | 3.49 | 2.31 | 34.00 |

EXAMPLE 4

To illustrate the effect of the pH maintained in the aqueous precipitation medium during the precipitation step, the synthesis of Example 1 was repeated. After the sulfation and acylation steps had been completed, at which point the sulfated cellulose acetate was dissolved in the reaction mixture, the reaction mixture was divided into seven equal portions designated 4A–4G respectively. Cellulose acetate sulfate resin was precipitated from each portion by adding that particular portion to an aqueous precipitation medium which was maintained at a specified pH by adding thereto, in amounts and at times needed, a solution of 50% aqueous sodium hydroxide. The precipitated products were washed and dried as before and analyzed. The pH during precipitation and results of the analysis are given in Table IV.

TABLE IV

| PORTION | PRECIP- ITATION pH | $(DS)SO_4=$ | $(DS)CH_3\overset{O}{\underset{\parallel}{C}}-$ | $(DS)OH-$ |
|---|---|---|---|---|
| 4A | 1.5 | 0.29 | 1.45 | 1.26 |
| 4B | 2.0 | 0.27 | 1.43 | 1.30 |
| 4C | 3.4 | 0.30 | 2.69 | 0.01 |
| 4D | 5.2 | 0.30 | 2.63 | 0.09 |
| 4E | 7.2 | 0.24 | 1.97 | 0.79 |
| 4F | 8.1 | 0.27 | 1.63 | 1.11 |
| 4G | 11.8 | 0.24 | 0.18 | 2.58 |

EXAMPLE 5

The procedure of Example 1 was repeated except that the sulfating mixture comprised 542.92 gms. of acetic anhydride, 87.55 grams of acetic acid, 102.66 grams of $Na_2SO_4$, and 67.12 grams of 98% by weight sulfuric acid. After recovery and purification, the product was analyzed and found to contain 5.40% by weight sulfur (corresponding to a degree of sulfate substitution of 0.49); 3.87% by weight sodium; and 27.3% by weight acetyl (corresponding to a degree of acetyl substitution of 1.84). Thus, it is seen that resins having higher degrees of sulfate substitution may be obtained An examination of the data in Table V shows that the amounts of acetic anhydride and sulfuric acid used during the acetylation reaction determine the amount of the acetyl substitution on the final product. The amount of sulfate substitution, which is directly proportional to the % sulfur, is also influenced, but to a much lesser degree, by variations in the amounts of acetic anhydride and sulfuric acid.

EXAMPLE 7

This example shows that alkali salts of sulfated cellulose esters can be prepared in a one-step procedure by reacting a slurry of woodpulp in an inert organic liquid with a reactant mixture comprising a sulfating agent and an acylating agent. Thus, in this process, the sulfation and acylation reactions take place together and the inconvenience and need for additional equipment associated with the two step sulfation and acylation procedure of Example 1 are eliminated. Once the cellulose ester sulfate is formed, it is recovered by precipitation in an aqueous precipitation medium maintained within the specified pH range, that is, at a pH of from about 3 to about 8.

400 grams of woodpulp (same as used in Example 1) and 2000 grams of glacial acetic acid were tumbled in a closed cylindrical reactor for 20.5 hours at 24° C. The resulting slurry was transferred to a jacketed Ross reactor equipped with suitable stirrer means. The following reagents were then added, with stirring, to the reactor in the following order: 1242.9 grams of acetic anhydride; 52.5 grams glacial acetic acid; 30.8 grams $Na_2SO_4$; and 52.15 grams of sulfuric acid (98% by weight). Cooling was applied during the above additions so that the temperature in the reactor did not exceed 32° C. Stirring was continued at 32° C for 2 hours, counting from the time the acetic anhydride was added to the reactor. The resulting product was precipitated at pH 5.2 using the precipitation method of Example 1. The resin was then purified and dried as in Example 1.

The resulting resin had the following analysis:
3.05% sulfur; 2.19% sodium; 31.4% acetyl; degree of sulfate substitution = 0.26; degree of acetyl substitution = 1.99; degree of hydroxyl substitution = 0.75.

This example shows that sodium cellulose acetate sulfate can be synthesized by a modified procedure in which the preparation of sodium acetyl sulfate in a separate reactor has been eliminated, and that the cellulose acetate sulfate can be successfully recovered from solution in the reaction mixture in which it was prepared by combining the reaction mixture with an aqueous base maintained at a specified pH.

The resins of this invention may be combined with other materials and will still exhibit their characteristic properties of water solubility and insolubility in aqueous salt solutions when cast into film form. For example, films have been made from combinations of alkali salts of sulfated cellulose esters with various plasticizers and with inexpensive fillers or extenders such as titanium dioxide, kaolin and acrylic resin. Such films, which may be cast from solutions of such mixtures in acetone/water or other suitable solvents, are less costly due to the presence therein of the inexpensive extenders. The films of this invention may be suitably plasticized with water soluble plasticizers such as the polyethylene glycols or with water insoluble plasticizers such as castor oil.

It will be apparent to one skilled in the art that many modifications to the invention are possible without departing from the scope and spirit thereof.

What is claimed is:

1. A process for the preparation of alkali cellulose ester sulfates having a degree of sulfate substitution of from about 0.1 to about 0.45 and a degree of acyl substitution of from 1.63 to 2.69 which comprises:
   a. slurrying the cellulose in an inert organic liquid;
   b. sulfating the cellulose by reacting the cellulosic slurry with a sulfating mixture comprising an alkali acetyl sulfate;
   c. esterifying the sulfated cellulose in a reaction mixture comprising said inert organic liquid, said sulfated cellulose, and an acylating agent; and
   d. precipitating said alkali cellulose ester sulfate by combining said reaction mixture with an aqueous precipitation medium maintained at a pH of from about 3 to about 8.

2. A process according to claim 1 wherein the pH is from about 3.5 to about 5.5.

3. A process according to claim 1 wherein said inert organic liquid is acetic acid.

4. A process according to claim 1 wherein said acylating agent is acetic anhydride.

5. In a process for recovering a cellulose ester sulfate having a degree of sulfate substitution of from about 0.1 to about 0.45 and a degree of acyl substitution of from 1.63 to 2.69 from a solution comprising an inert organic liquid and said cellulose ester sulfate, the step which comprises combining said solution with an aqueous precipitation medium maintained at a pH of from about 3 to about 8.

6. The process of claim 5 wherein the pH is from about 3.5 to about 5.5.

7. The process of claim 5 wherein said pH range is maintained by adding an aqueous solution of a base selected from the group consisting of alkali metal hydroxides, salts of alkali metal hydroxides with weak acids, and ammonium hydroxide.

* * * * *